United States Patent [19]

Gehman et al.

[11] 4,196,190

[45] Apr. 1, 1980

[54] ACRYLIC HAIR SETTING RESINS HAVING HIGH RESISTANCE TO MOISTURE AND RAPID REMOVABILITY FROM THE HAIR WITH SHAMPOO

[75] Inventors: David R. Gehman, Harleysville; William A. Kirn, Abington, both of Pa.

[73] Assignee: Rohm and Haas Company, Philadelphia, Pa.

[21] Appl. No.: 867,732

[22] Filed: Jan. 9, 1978

Related U.S. Application Data

[63] Continuation-in-part of Ser. No. 706,336, Jul. 19, 1976.

[51] Int. Cl.² ........................ A61K 7/11; C08F 16/04
[52] U.S. Cl. .............................. 424/47; 260/33.4 R; 424/DIG. 1; 424/DIG. 2; 424/71; 424/81; 526/317; 526/320
[58] Field of Search ................. 424/DIG. 1, DIG. 2, 424/47, 71, 81; 526/317, 320; 260/33.4 R

[56] References Cited

U.S. PATENT DOCUMENTS

| | | | |
|---|---|---|---|
| 3,468,836 | 9/1969 | Sekmakas | 260/33.6 SB |
| 3,577,517 | 5/1971 | Kubot et al. | 424/47 |
| 3,660,561 | 5/1972 | Shepherd et al. | 424/47 |
| 3,865,904 | 2/1975 | Wingler et al. | 526/317 X |
| 3,925,542 | 12/1975 | Viout et al. | 424/47 |
| 3,970,633 | 7/1976 | Miller et al. | 526/317 X |

FOREIGN PATENT DOCUMENTS 1,406,979  9/1975  United Kingdom .................. 424/71

*Primary Examiner*—Bernard Helfin
*Assistant Examiner*—Vera C. Clarke

[57] ABSTRACT

Acrylic polymer solutions having superior properties when used as hair setting or holding resins are disclosed. Specific polymers disclosed are derived from (1) alkyl acrylates with 2–8 carbon alkyl groups, (2) methyl methacrylate, (3) hydroxyethyl methacrylate, and (4) methacrylic acid in proportions yielding a film forming resin readily soluble in shampoo, with a Tg between about 40° C. and 80° C., a molecular weight between about 25,000 and 250,000 and not more than 50 ppm of unreacted alkyl acrylate monomer.

10 Claims, No Drawings

ACRYLIC HAIR SETTING RESINS HAVING HIGH RESISTANCE TO MOISTURE AND RAPID REMOVABILITY FROM THE HAIR WITH SHAMPOO

CROSS REFERENCE TO RELATED APPLICATION

This application is a continuation-in-part of our prior copending application Ser. No. 706,336, filed July 19, 1976, now abandoned.

The present invention relates to an improved class of cosmetic hair setting resins producing high resistance to moisture, good curl retention, and excellent shampoo removability. Specifically, the resins are acrylic copolymers of alkyl acrylates, methyl methacrylate, hydroxyethyl methacrylate and methacrylic acid.

Cosmetic hair spray resins are polymers which when suitably formulated are applied to the hair to impart curl retention and "hold" to the coiffure. The first synthetic resin, polyvinyl pyrrolidone, was introduced in 1953 and is still employed in hair sprays. Its performance has been shown to be marginal, at best, in that it offers only fair curl retention and at conditions of high relative humidity is extremely tacky. Recently developed copolymers of polyvinyl pyrrolidone/vinyl acetate and polyvinyl ether/maleic anhydride offer improved curl retention but still impart a sticky feel to the hair at high relative humidity. Since hair sprays should be readily removable by shampoo washing, this problem is a direct result of the compromise of adequate shampoo removability with water and humidity resistance.

Acrylic solution copolymers have also been marketed for use as hair sprays. However, such products have never been commercially successful, in part because of the offensive monomer odor which accompanies these products. Some of the more recent developments in acrylic hair setting copolymers may be seen by reference to: U.S. Pat. Nos. 3,577,517 and 3,577,518 (May 4, 1971); U.S. 3,453,245 (July 1, 1969) and 3,245,932 (Aug. 12, 1966).

We have now discovered that an optimum hydrophobe/hydrophile balance through proper acrylic monomer selection will produce a hair spray resin which imparts improved curl retention at high relative humidity, superior moisture resistance, excellent shampoo removability and good aesthetic properties to the hair. Such a balance of performance properties is obtainable through the judicious incorporation of hydrophilic and hydrophobic acrylic monomers in the same backbone. A polymer of this preferred composition, when incorporated into an aerosol or pump type hair spray formulation has been shown to offer an improved performance profile over current competitive products. Further, by reduction of the unreacted alkyl acrylate monomer in the final copolymer, we have produced a composition which avoids the offensive odors of the prior art acrylate hair resins.

The copolymers of the invention comprise (1) between about 10% and 30% by weight of an alkyl acrylate having a straight or branched chain alkyl group of 2-8 carbon atoms, and preferably 2 to less than 8 (2) between about 41% and 60% by weight of methyl methacrylate, (3) between about 5% and 20% by weight of hydroxyethyl methacrylate, and (4) between about 10% and 30%, and preferably 12-30%, by weight of methacrylic acid. To achieve the superior properties of the cosmetic hair spray compositions disclosed herein the above proportions of the various acrylic monomers must be selected to yield a polymer having a calculated glass transition temperature (Tg) between about 40° C. and 80° C. preferably about 45° C. to 75° C., and a molecular weight range between about 25,000 and 250,000, preferably between about 50,000 and 150,000. A most preferred polymer has a Tg of about 55° C. and a molecular weight of about 70,000. For cosmetic use, the polymers of the invention must also be relatively odor free. We have found that odor may be minimized substantially by reducing the amount of unreacted alkyl acrylate monomer, particularly butyl acrylate present in the final polymer composition, to not more than 50 ppm.

In general, the alkyl acrylate component of the copolymer plasticizes or reduces the brittleness of the copolymer film, the methyl methacrylate provides hardness to give the film its non-tacky holding properties and the functional monomers (hydroxyethyl methacrylate (HEMA) and methacrylic acid (MAA)) produce shampoo removability. The preferred alkyl acrylate is butyl acrylate with shorter chain acrylates, e.g., ethyl acrylate being preferred over long chain acrylates, e.g., 2-ethylhexyl acrylate. A combination of the functional monomers, such as HEMA/MAA in a proportion of 10%/18% by weight of the copolymer, is much preferred over either alone. Increasing the MAA level above 18% further improves shampoo removability but begins to adversely affect curl retention performance. A HEMA level of approximately 10% is the preferred level as will be seen hereinafter from the data relating to free film and curl retention studies. Higher levels of HEMA produce adverse effects on free films at high relative humidity as well as lower curl retention.

The copolymers may be prepared by conventional methods known heretofore in the art. Most desirably, the copolymers are prepared by emulsion polymerization followed by freeze or spray drying to synthesize a polymer having extremely low residual monomer. Suitable emulsion polymerization methods are disclosed in U.S. Pat. Nos. 3,245,932 and 3,453,245 which teachings are hereby incorporated herein by reference. One particularly effective method involves a gradual addition, thermal procedure using an initiator (e.g., ammonium persulfate), a surfactant, a chain regulating agent (e.g., 1.0% bromotrichloromethane) and a redox chase system (e.g., t-butylhydroperoxide/isoascorbic acid). When using butyl acrylate, the characteristic odor of BA is detected before the chase step, but a single chase has sufficed to eliminate it. A second chase is nevertheless not generally detrimental to the product if otherwise desired. Typically, BA odor cannot be detected at a level of 30-40 ppm in an emulsion.

In formulating the polymers of the invention for consumer use by direct application to the hair, a variety of neutralizing agents, perfumes, solvents, polypeptides, silicones (e.g., polysiloxanes), plasticizers, propellants, and other adjuvents are often desirably combined with the polymers. The polymers are generally compatible with the materials used heretofore in hair spray formulations, such as those disclosed in U.S. Pat. Nos. 3,577,517 and 3,577,518, both issued May 4, 1971; and 3,912,808 issued Oct. 14, 1975.

Normally, the preformed polymer is dissolved in a suitable solvent such as water, ethyl alcohol, methyl alcohol, propyl alcohol, isopropyl alcohol, dimethyl formamide, dimethyl sulfoxide, or the like, after which an amine neutralizing agent is added. Among the amine neutralizing agents known in the art and useful by this invention are: 2-amino, 2-methyl, 1,3 propanediol (AMPD); 2-amino, 2-methyl, 1-propanol (AMP); N, N, dimethyl, 2-amino, 2-methyl, 1-propanol (DMAMP); mono-isopropanolamine; triisopropanolamine; ethanolamine; and morpholine. A suitable group of plasticizers includes long chain alcohols and glycols, salts of fatty acids, and ethoxylated esters, ethers and alcohols.

When the polymer of the invention is to be formulated in an aerosol composition a propellant is required. Compressed gases such as carbon dioxide, nitrous oxide and nitrogen; fluorinated hydrocarbons such as dichlorodifluoromethane, trichlorofluoromethane, etc.; and liquid volatile hydrocarbons such as propane, N-butane, isobutane, etc. may all be used alone or in suitable combinations. As a rule the propellant comprises 30–70% of the total formulation, although higher and lower percentages may also be used.

Some typical formulations (used in the formulated products disclosed in the following examples) which may be made with the polymers of the invention are as follows.

| | Aerosol Hair Spray | |
| --- | --- | --- |
| | Regular (% by weight) | Hard to Hold (% by weight) |
| Polymer "C" (Table I below) | 1.000 | 2.000 |
| AMP | 0.091 | 0.182 |
| SDA-40 | 33.909 | 32.818 |
| Freon 11/Freon 12 60/40 | 65.000 | 65.000 |
| Perfume | q. s. | q. s. |
| | Non-Aerosol Hair Spray | |
| | Regular (% by weight) | Hard to Hold (% by weight) |
| Polymer "C" (Table I below) | 3.000 | 4.000 |
| AMP | 0.273 | 0.364 |
| SDA-40 | 96.727 | 95.636 |
| Perfume | q. s. | q. s. |

Polymer C exhibits a wide range of solubility in SDA-40/water solutions at all levels of neutralization and is generally compatible with varying levels of SDA-40 (a cosmetic grade of ethanol), Freon 11 and Freon 12.

The following specific examples illustrate preferred methods and embodiments of the invention.

EXAMPLE 1

The preparation of a cosmetic copolymer containing 25% butyl acrylate (BA), 47% methyl methacrylate (MMA), 10% HEMA and 18% MAA is illustrated hereinafter.

Raw Materials

Butyl Acrylate
Methyl Methacrylate
Hydroxyethyl Methacrylate
Methacrylic Acid
Sipon WD (surfactant)
Bromotrichloromethane (chain regulator)
Ammonium Persulfate (initiator)
t-Butyl Hydroperoxide
iso-Ascorbic Acid

Recipe for a Five Gallon Batch

1. Equipment

A 5 gallon glass kettle was equipped with addition pump, condenser, stirrer, thermometer, and nitrogen sparge. Means for heating and cooling were provided.

2. Material Charges—Emulsion and Kettle

| Material | Emulsion | Kettle |
| --- | --- | --- |
| Deionized Water | 2120 g. | 8780 g. |
| Sipon WD | 21.7 g. | 15.7 g. |
| Butyl Acrylate | 1875 g. | — |
| Methyl Methacrylate | 3520 g. | — |
| Hydroxyethyl Methacrylate | 750 g. | — |
| Bromotrichloromethane | 75 g. | — |
| Methacrylic Acid | 1350 g. | — |

3. Catalyst

Ammonium Persulfate—15 g. in 250 g. deionized water

4. Chase t-Butyl Hydroperoxide—3.3 g. in 250 g. deionized water iso-Ascorbic Acid—4.4 g. in 250 g. deionized water

Procedure

1. Kettle
  a. Charge deionized water and Sipon WD.
  b. Place kettle under nitrogen sparge; stir and heat system to 83° C.
2. Emulsion
  a. Charge deionized water and Sipon WD.
  b. Add butyl acrylate, methyl methacrylate, and hydroxyethyl methacrylate, emulsify after each addition.
  c. Add bromotrichloromethane and emulsify.
  d. Add methacrylic acid and emulsify.
3. Polymerization
  a. With kettle at 83° C. and under nitrogen, add 650.0 g. of the emulsion as a preform and stir for 5 minutes.
  b. With system at 83° C., add the catalyst solution and stir for 15 minutes. Initial exotherm controls at 86° C. Hold the system at 85° C. during remainder of reaction.
  c. Start the 100 min. addition of the remainder of the monomer emulsion (a rate of about 96 ml/min. is required for the 5 gallon run described).
  d. After completion of the monomer addition, hold system at 85° C. for 15 minutes.
  e. Add chase and stir for 45 minutes.
  f. Cool to 25° C.; Filter.

| Data for Typical Preparation: | |
| --- | --- |
| pH: | 1.8 |
| % Solids: | 40.2 |
| Brookfield Viscosity, cps (2,60)* | 17.5 |
| Gum, wet: | Trace |
| Residual BA, %: | 0.003 |

*Spindle #2 at 60 rpm

EXAMPLE 2

Following the general method of Example 1, a number of polymers were prepared as freeze dried emulsions (as a means of removing water and reducing objectionable residual monomer). The compositions, chain regulator amounts (% BTM—bromotrichloromethane), and Tg °C. are set forth in the following table.

TABLE I

| Polymer Identification | Composition | % BTM | Tg °C.* |
|---|---|---|---|
| A | BA/MMA/HEMA/MAA/30/42/10/18 | — | 42 |
| B | BA/MMA/MAA/25/57/18 | 1.0 | 55 |
| C | BA/MMA/HEMA/MAA/25/47/10/18 | 1.0 | 52 |
| D | BA/MMA/MAA/26.5/50.5/23 | 1.0 | 55 |
| E | BA/MMA/HEMA/MAA/24.5/52.5/5/18 | 1.0 | 52 |
| F | BA/MMA/HEMA/MAA/27.5/44.5/28 | 1.0 | 55 |
| G | BA/MMA/HEMA/MAA/21/41/20/18 | 1.0 | 52 |
| H | BA/MMA/MAA/30/52/18 | 1.0 | 45 |
| I | BA/MMA/HEMA/MAA/19/53/10/18 | 1.0 | 64 |
| J | BA/MMA/HEMA/MAA/13/59/10/18 | 1.0 | 79 |

*Calculated Tg's herein (using e. g., the Fox equation) are based upon assumed Tg's for the individual components as follows:

| Homopolymer | Tg of high MW Homopolymer |
|---|---|
| BA | −54° C. |
| MMA | 105° C. |
| HEMA | 55° C. |
| MAA | 200° C. | and without neutralization. Polymers B, D and F (from Table I) having Tg's of 55° C. were selected for testing and polymer H, having a Tg of 45° C., was selected as a control. The results are summarized in the following table.

TABLE II

FILM PROPERTIES AT Tg = 55° C.

| Sample | Neutralization (AMPD) | *Hygroscopicity 90% RH/28° C. | | | | | | **Water Resistance (24 hrs.) | Shampoo Solubility | |
|---|---|---|---|---|---|---|---|---|---|---|
| | | 15″ | 30″ | 1hr. | 2hrs. | 4hrs. | 8hrs. | | Prell | Protein 21 |
| H | 75% | 2 | 2 | 2 | 2 | 3 | 3 | 2 (2 min.) | 4 min. | 1.3 hrs. |
| B | 0% | 1 | 1 | 1 | 1 | 1 | 1 | 1 | >6 hrs. | >6 hrs. |
|  | 50% | 1 | 1 | 1 | 2 | 2 | 2 | 1 | 21 min. | 6 hrs. |
|  | 75% | 2 | 2 | 2 | 2 | 2 | 2 | 1 | 6 min. | 5 hrs. |
| D | 0% | 1 | 1 | 1 | 1 | 1 | 1 | 1 | >6 hrs. | >6 hrs. |
|  | 50% | 1 | 1 | 1 | 2 | 2 | 2 | 1 | 4 min. | 40 min. |
| F | 0% | 1 | 1 | 1 | 1 | 1 | 1 | 1 | >6 hrs. | >6 hrs. |
|  | 20% | 1 | 1 | 1 | 2 | 2 | 2 | 1 | 6 min. | 20 min. |
|  | 50% | 2 | 2 | 3 | 3 | 3 | 3 | 1 | 2 min. | 7 min. |

Legend
*Hygroscopicity
1 = No effect
2 = Slight tack
3 = Moderate tack
4 = Loss of film intergrity; film becomes soupy
**Water Resistance
1 = No change
2 = Film whitens
3 = Film disintegrate
4 = Film solubilizes The Prell and Protein shampoo solubility data in Table II above refer to the time required for a free film to dissolve in Prell or Protein shampoo diluted 1:4 with water. The results indicate that increasing MAA concentration will greatly improve shampoo solubility. However, this result is clouded by the fact that a polymer containing 28% MAA, when neutralized 50% requires the same amount of amine as a polymer containing 18% MAA neutralized 75%. A comparison of the shampoo solubility data of sample B neutralized 75% vs sample F neutralized 50% shows that the higher acid containing polymer F gives greater shampoo solubility. These findings are substantiated by additional test results.

EXAMPLE 4

Using the procedure of Example 3 above, other polymers from Table I were tested. The results are summarized in the following table.

TABLE III

FILM PROPERTIES

| Sample | Neutralization (AMPD) | Hygroscopicity 90% RH/28° C. | | | | | | Water Resistance | Shampoo Solubility | |
|---|---|---|---|---|---|---|---|---|---|---|
| | | 15′ | 30′ | 1 hr. | 2 hrs. | 4 hrs. | 8 hrs. | | Prell | Protein 21 |
| H | 75% | 2 | 2 | 2 | 2 | 3 | 3 | 2 (2 min) | 4 min. | 1.3 hrs. |
| B | 0% | 1 | 1 | 1 | 1 | 1 | 1 | 1 (24 hrs) | >6 hrs. | >6 hrs. |
|  | 50% | 1 | 1 | 1 | 2 | 2 | 2 | 1 (24 hrs) | 21 min. | 6 hrs. |
|  | 75% | 2 | 2 | 2 | 2 | 2 | 2 | 1 (24 hrs) | 6 min. | 5 hrs. |
| E | 0% | 1 | 1 | 1 | 1 | 1 | 1 | 1 (24 hrs) | >6 hrs. | >6 hrs. |
|  | 50% | 1 | 1 | 1 | 2 | 2 | 2 | 1 (24 hrs) | 10 min. | 6 hrs. |
| C | 0% | 1 | 1 | 1 | 1 | 1 | 1 | 1 (24 hrs) | >6 hrs. | >6 hrs. |
|  | 50% | 2 | 2 | 2 | 2 | 2 | 2 | 1 (24 hrs) | 4 min. | 40 min. |
| G | 0% | 1 | 1 | 1 | 1 | 1 | 1 | 2 (30 min) | 2.5 hrs. | >6 hrs. |
|  | 20% | 1 | 1 | 1* | 1 | 1 | 1 | 2 (10 min) | 10 min. | 2.5 hrs. |
|  | 50% | 2 | 2 | 2* | 2 | 2 | 3 | 2 (10 min) | 1 min. | 8 min. |
| A | 0% | 1 | 1 | 1 | 1 | 1 | 1 | 1 (24 hrs) | >6 hrs. | >6 hrs. |
|  | 50% | 1 | 1 | 2 | 2 | 2 | 2 | 1 (24 hrs) | 29 min. | 6 hrs. |
|  | 75% | 2 | 2 | 2 | 2 | 3 | 3 | 1 (24 hrs) | 14 min. | 2 hrs. |

*Polymer film turned white after 1 hr at 90% RH.

EXAMPLE 3

Several polymers of Table I, above, were formed into films and tested with regard to their properties, with The free film tests disclosed above in Examples 3 and 4 with results reported in Tables II and III were conducted to determine hygroscopicity, water sensitivity and shampoo solubility. These tests were conducted by casting polymer films from ethanolic solutions on standard vinyl floor tile. The solutions were prepared at 30% solids and cast using a 10 mil drawdown block. The films were permitted to air dry before peeling them from the tile. They were then cut into $\frac{1}{4}''$ by $\frac{1}{2}''$ pieces and placed in sample vials in a "dry box" (10% RH) overnight prior to testing.

1. Hygroscopicity Test

Hygroscopicity testing was conducted by placing the free films on a glass plate in a 90% relative humidity 28° C. environment. The chamber used for these tests was a Hotpack "Incubator". The films were examined with the aid of a micro spatula after 15 minutes, 30 minutes, 1 hour, 2 hours, 4 hours, and 8 hours for any evidence of hydroplasticization and tack. Results were reported as follows:

| Rating | Observation |
| --- | --- |
| 1 | No effect |
| 2 | Slight tack or adhesion to glass |
| 3 | Moderate tack or adhesion to glass |
| 4 | Complete loss of film integrity; film becomes soupy |

2. Water Resistance Test

Water resistance was measured by adding de-ionized water to vials containing samples of the free films after they had equilibrated in the "dry box" overnight. Any changes in the film were recorded as was the time of the change. Changes in the film in water were recorded as follows:

| Rating | Observation |
| --- | --- |
| 1 | No change |
| 2 | Whitening of the film |
| 3 | Disintegration of the film |
| 4 | Dissolution of the film |

3. Shampoo Solubility Test

Shampoo solubility was measured by adding aqueous solutions of "Prell Shampoo" and "Protein 21 Shampoo for Oily Hair" diluted 1:4 to vials containing samples of the free films. As prepared, the Prell shampoo has a pH of 7.5 while the Protein 21 a pH of 6.5. The time required for the film to completely dissolve was recorded.

EXAMPLE 5

Curl retention studies on the polymers of the invention were conducted using 1.5 gm swatches of brown virgin hair cemented together at the root end and trimmed to a length of 22 cm. Each swatch was prepared for testing by first washing in Prell shampoo solution 1:4 at 130° F. The swatches were then exhaustively rinsed in hot tap water and combed several times to remove kinks and excess water. A 100 gm weight was then attached to the root end with the free end placed on a 1" O. D. glass spool and the swatch coil wound, making sure the weight hung freely. A clip was used for each swatch to prevent its uncurling. The swatches were then permitted to dry at 50° C. for one hour followed by 16 hours at room temperature. The spools were then removed and each swatch was formed into a spiral configuration. Each curl was then weighed on an analytical balance. The test hair spray formulation prepared at 4% solids was sprayed onto each curl via a "Preval" aerosol unit at a distance of 12 inches for 4 seconds while the curl was rotating through its long axis at a rate of 60 rpm.

The curls were then reweighed prior to testing to determine the coating weight. The curls were placed in a controlled temperature and relative humidity environment set at 28° C. and 90% RH. The initial length of each curl was measured. Measurements were recorded every half hour for three hours and after 21 hours. The percent curl retention was calculated from the following:

$$\text{Percent Curl Retention} = \frac{L_e - L_t}{L_e - L_o} \times 100$$

where
$L_e$=length of the hair swatch fully extended
$L_o$=length of the hair swatch initially
$L_t$=length of the hair swatch after exposure to the test conditions after some time T To compare a preferred polymer of the invention against a commercially available polymer and a popular hair spray, the polymer composition of Example 1, above (polymer "C" in Table I) containing 25% BA, 47% MMA, 10% HEMA and 18% MAA was formulated in a 4% by weight solution of the polymer in SDA-40 (cosmetic grade of ethanol) using 50% neutralization with AMP. Using the commercially available hair spray polymer Amphomer (a product of National Starch Company), which showed excellent curl retention properties upon preliminary testing, a second 4% spray solution in SDA-40, 50% neutralized with AMP, was also prepared. These compositions and a popular hair spray of good performance characteristics were tested for curl retention by the preceeding method.

TABLE IV

| Sample | Average Coating (mgs.) | Percent Curl Retention (90% R. H. - 85° F.) | | | |
| --- | --- | --- | --- | --- | --- |
| | | 1 hr. | 2 hrs. | 3 hrs. | 21 hrs. |
| Polymer of Example 1 | 20 | 90 | 88 | 88 | 88 |
| Polymer of Example 1 | 57 | 91 | 89 | 89 | 89 |
| Amphomer | 20 | 82 | 82 | 82 | 82 |
| Amphomer | 57 | 84 | 84 | 84 | 84 |
| Popular Hair Spray | 22 | 67 | 60 | 60 | 60 |
| Popular Hair Spray | 77 | 78 | 74 | 74 | 71 |

The data of Table IV show the impressive curl retention of polymers of the invention, even at a low coating weight of 20 mgs.

EXAMPLE 6

Instron tensile strength measurements were conducted on films cast from several hair spray formulations including Polymer C of Table I. After the films were cast they were permitted to dry at room temperature. Tensile strength evaluations were conducted on the films after conditioning at 50% and 90% relative humidity for 5 hours prior to actual testing. (Crosshead speed of the Instron Tester was 0.2 inches/minute with initial jaw opening of 0.5 inches).

| Formulation | Conditioning Relative Humidity | % Elongation At Failure | Maximum Load (kg/in$^2$) |
|---|---|---|---|
| Polymer C (Table I above) | 50% | 7% | 542 |
| | 90% | 8% | 567 |
| Miss Breck Superhold | 50% | 7% | 520 |
| | 90% | 558% | 310 |
| Final Net (Clairol, Inc.) | 50% | 11% | 574 |
| | 90% | 363% | 346 |

The above data demonstrate the ability of the novel polymers of the invention to maintain excellent tensile strength with low hydroplasticity (film elongation) at high relative humidity.

EXAMPLE 7

Following the method taught in Example 5, each of the polymer materials shown in Table I above was tested a number of times for curl retention at 90% R. H. The results are set forth in the following table.

TABLE V

| Polymer (Table I) | Neutralization | Number of Tests | Curl Retention at 90% RH 28° C. | | | | | | | |
|---|---|---|---|---|---|---|---|---|---|---|
| | | | 1 hr. | | 2 hrs. | | 3 hrs. | | 21 hrs. | |
| | | | Avg. | % Dev | Avg. | % Dev | Avg. | % Dev | Avg. | % Dev |
| H | 75% AMPD | 6 | 88 | ±2 | 87 | ±2 | 85 | ±2 | 83 | ±3 |
| B | 75% AMPD | 8 | 93 | ±1 | 92 | ±1 | 90 | ±1 | 90 | ±1 |
| D | 50% AMPD | 6 | 91 | ±1 | 91 | ±1 | 91 | ±1 | 88 | ±2 |
| F | 33% AMPD | 8 | 92 | ±1 | 90 | ±1 | 87 | ±2 | 87 | ±2 |
| E | 50% AMPD | 7 | 90 | ±2 | 90 | ±2 | 90 | ±2 | 85 | ±2 |
| C | 50% AMPD | 10 | 95 | ±1 | 94 | ±1 | 92 | ±1 | 91 | ±1 |
| G | 40% AMPD | 8 | 90 | ±2 | 86 | ±2 | 84 | ±2 | 81 | ±3 |
| A | 50% AMPD | 6 | 92 | ±1 | 91 | ±1 | 89 | ±2 | 89 | ±2 |

The above results show that with increasing MAA levels, curl retention appears to be slightly adversely affected. However, it must be considered that a certain minimum MAA level is required to obtain adequate shampoo removability of the polymer film. Reviewing the performance of the HEMA containing polymers, it may be seen that a maximum curl retention is obtained with 10% HEMA, as in Polymer C. This polymer also provided an exceptional balance of free film properties when neutralized with an organic amine.

Formulation of the polymer in a cosmetically suitable mixture is within the ordinary skill of the cosmetic chemists' art. In order to achieve sufficient water and/or shampoo solubility it is necessary to neutralize with one or more of the amine neutralizers disclosed herein. A high level of neutralization is normally required (40-100%, preferably 50-80%) if the polymer is to be formulated in an aqueous medium such as a hair setting lotion. For purposes of such formulations, water is intended to be embraced within the term "organic solvent" as used herein. The least amount of neutralization consistent with the attainment of the desirable properties for the particular formulation is preferred, since many of the more desirable characteristics of the polymer are sacrificed (e.g., humidity resistance, tensile strength) by over neutralization.

We claim:

1. A hair setting composition for application to human hair to cosmetically set and hold the same for a reasonable period of time and which is readily removable therefrom by shampoo treatment which comprises (A) a film forming copolymer of (1) 10-30% by weight of an alkyl acrylate having a straight or branched chain alkyl group of 2 to less than 8 carbon atoms or mixture thereof, (2) 41-60% by weight of methyl methacrylate, (3) 5-20% by weight of hydroxyethyl methacrylate, and (4) 12-30% methacrylic acid, which copolymer has a calculated glass transition temperature, Tg, within the range of about 40°-80° C., a molecular weight within the range of about 25,000 to 250,000, and not more than about 50 ppm of unreacted alkyl acrylate monomer, and (B) a cosmetically acceptable organic solvent for said film forming copolymer, wherein (A) is dissolved in (B) in an amount of 1 to 15% by weight of the composition with the required amount of organic amine neutralizer to achieve acceptable performance.

2. The composition of claim 1 wherein the alkyl acrylate component of the film forming copolymer (A) is n-butyl acrylate.

3. The composition of claim 1 wherein the molecular weight range of the copolymer is between 50,000 and 150,000.

4. The composition of claim 1 wherein the calculated Tg is within the range of about 45°-75° C.

5. The composition of claim 1 wherein the film forming copolymer contains the following components in approximately the indicated proportions by weight:

| butyl acrylate | 25% |
|---|---|
| methyl methacrylate | 47% |
| hydroxyethyl methacrylate | 10% |
| methacrylic acid | 18% |

6. The composition of claim 1 wherein the methacrylic acid component of the film forming copolymer comprises about 18% by weight of the copolymer.

7. The composition of claim 1 wherein the hydroxyethyl methacrylate component of the film forming copolymer comprises about 10% by weight of the copolymer.

8. The composition of claim 5 wherein the film forming copolymer has a molecular weight of about 70,000.

9. An aerosol hair spray composition comprising between 30 and 70 weight percent of components A and B of claim 1 and between 70 and 30 weight percent of a spraying agent selected from the group consisting of halogenated hydrocarbons, compressed gases, volatile hydrocarbons and mixtures thereof.

10. A water insoluble, shampoo soluble hair setting polymer which comprises (a) 10-30% by weight of an alkyl acrylate having a straight or branched chain alkyl group of 2 to less than 8 carbon atoms or mixtures thereof (b) 41-60% by weight of methyl methacrylate, (c) 5-20% by weight of hydroxyethyl methacrylate and (d) 12-30% by weight of methacrylic acid.

* * * * *